United States Patent
Donovan et al.

(10) Patent No.: US 7,179,837 B1
(45) Date of Patent: Feb. 20, 2007

(54) USE OF PRENYLATED FLAVONES

(75) Inventors: Robert Mark Donovan, Shambrook (GB); Martin Richard Green, Shambrook (GB); Maria Catherine Tasker, Shambrook (GB); Paula Rachel Yates, Shambrook (GB)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 428 days.

(21) Appl. No.: 10/453,012

(22) Filed: Jun. 3, 2003

Related U.S. Application Data

(62) Division of application No. 09/957,325, filed on Sep. 20, 2001, now Pat. No. 6,589,982.

(30) Foreign Application Priority Data

Sep. 22, 2000 (EP) .................. 00308359

(51) Int. Cl.
*A61K 31/35* (2006.01)
*A01N 63/04* (2006.01)

(52) U.S. Cl. .................. 514/456; 514/886; 514/25; 424/195.15; 424/195.16

(58) Field of Classification Search ................ 514/456, 514/886, 25; 424/195.15–16
See application file for complete search history.

(56) References Cited

U.S. PATENT DOCUMENTS

| | | | |
|---|---|---|---|
| 6,136,849 | A | 10/2000 | Hoffmann et al. |
| 6,194,469 | B1 | 2/2001 | Nair et al. |
| 6,399,579 | B1 | 6/2002 | Lenoble et al. |
| 6,589,982 | B2 | 7/2003 | Donovan et al. |

FOREIGN PATENT DOCUMENTS

| | | |
|---|---|---|
| EP | 667 289 | 2/1995 |
| GB | 2330 076 | 4/1999 |
| JP | 83009084 | 2/1983 |
| WO | 00/33824 | 6/2000 |
| WO | 01/03687 A2 | 1/2001 |

OTHER PUBLICATIONS

Steven et al., Quantitative analysis of xanthohumol and related prenylflavonoinds . . . , (Abstract only), Journal of Chromatography, 1999, vol. 832(1+2), pp. 97-107.*
Randoin et al., Do the water-soluble B vitamins of yeast . . . , Abstract only, Compt. rend. 1926, vol. 182, pp. 1564-1566.*
Walker et al., Health-promoting ingredients in beer, abstract only, Technical Quarterly-Master Brewers Association of the Americas(2000), vol. 37(s), pp. 301-305.*
Miranda et al., ANtimutagenic activity of prenylated flavonoids from hops . . . , (abstract only), Proceddings of the American Association for Cancer Research Annual Meeting, (Mar. 2000), Co. 41, pp. 847.*
Stevens et al., Fate of canthohumol and related prenylflavonoids from hops to beer.(abstract only), Journal of Agricultural and Food chemistry, (Jun. 1999), vol. 47, No. 6, pp. 2421-2428.*
Ito et al., A New falvonoid and other new conponents from citrus plants. (abstract only), chemical and Pharmaceutical bulletin(tokyo), 1988 vol. 36, No. 9 pp. 3292-3295.*
European Search Report dated Mar. 21, 2001 (EP 00 30 8359).
European Search Report dated Dec. 21, 2001 (EP 01 20 3414).
Kimura Y et al., "*Effects of Flavonoids and Related Compounds from Mulberry Tree Morus-Alba on Arachidonate Metabolism in Rat Platelet Homogenates*", Chemical & Pharmaceutical Bulletin, vol. 34, No. 3, 1986, pp. 1223-1227.
J. Tekel et al., "*Determination of the hop derived phytoestrogen, 8-prenylnaringenin, in beer by gas chromatography/mass spectrometry*", Journal of Agriculture an Food Chemistry, vol. 47, No. 12, 1999, pp. 5059-5063.
Stevens J. F. et al., "*Quantitative analysis of xanthohumol and related prenylflavonoids in hops and beer by liquid chromatography-tandem mass spectrometry*", Journal of Chromatography A,NL,Elsevier Science, vol. 832, No. 1-2, 1999, pp. 97-107.
Kitaoka Masahiro et al., "*Prenylflavonoids, A new class of nonsteroidal phytoestrogen, Part 1. Isolation of 8-preylnaringenin and an initial study on its structure activity relationship*", Planta Medica, vol. 64, No. 6, 1998, pp. 511-515.
JP 04202138, Patent Abstracts of Japan, vol. 106, No. 537, 1992.
JP 11246387, Patent Abstracts of Japan, vol. 1999, No. 14.
Baron Denis et al., "*Isoprenylated flavonoids: A survey*", Photochemistry, vol. 43, No. 5, 1996, pp. 921-982.
Database Biosis (Online), Biosciences Information Service, Tahara Satoshi et al., "*Prenylated flavonoids in the roots of yellow lupin*", and Phytochemistry, vol. 36, No. 5, 1994, pp. 1261-1271.
XP-002186324 (abstract—"Antiplatelet Activity of Some Prenylflavonoids", *Biochemical Pharmacology*, vol. 45, No. 2, 1993, pp. 509-512).
XP-002186326 (abstract—"In-Vitro Immunopharmacological Profile of the Plant Flavonoid Baohuoside-1", *International Journal of Immunopharmacology*, vol. 13, No. 2-3, 1991, pp. 129-134).
Antiproliferative and Cytotoxic Effects of Prenylated Flavonoids from Hops (*Humulus lupulus*) in Human Cancer Cell Lines, *Food and Chemical Toxicology*, vol. 37, 1999, pp. 271-285.
"Chemistry and Biology of Hop Flavonoids", *American Society of Brewing Chemists, Inc.*, 56(4), 1998, pp. 136-145.

* cited by examiner

*Primary Examiner*—Vickie Kim
(74) *Attorney, Agent, or Firm*—Michael P. Aronson

(57) ABSTRACT

Flavones with an isoprenyl group in the 8-position possess very good anti-inflammatory properties and can also be used to treat/prevent/cure skin-disorders when applied in food compositions.

4 Claims, 3 Drawing Sheets

Figure 1:
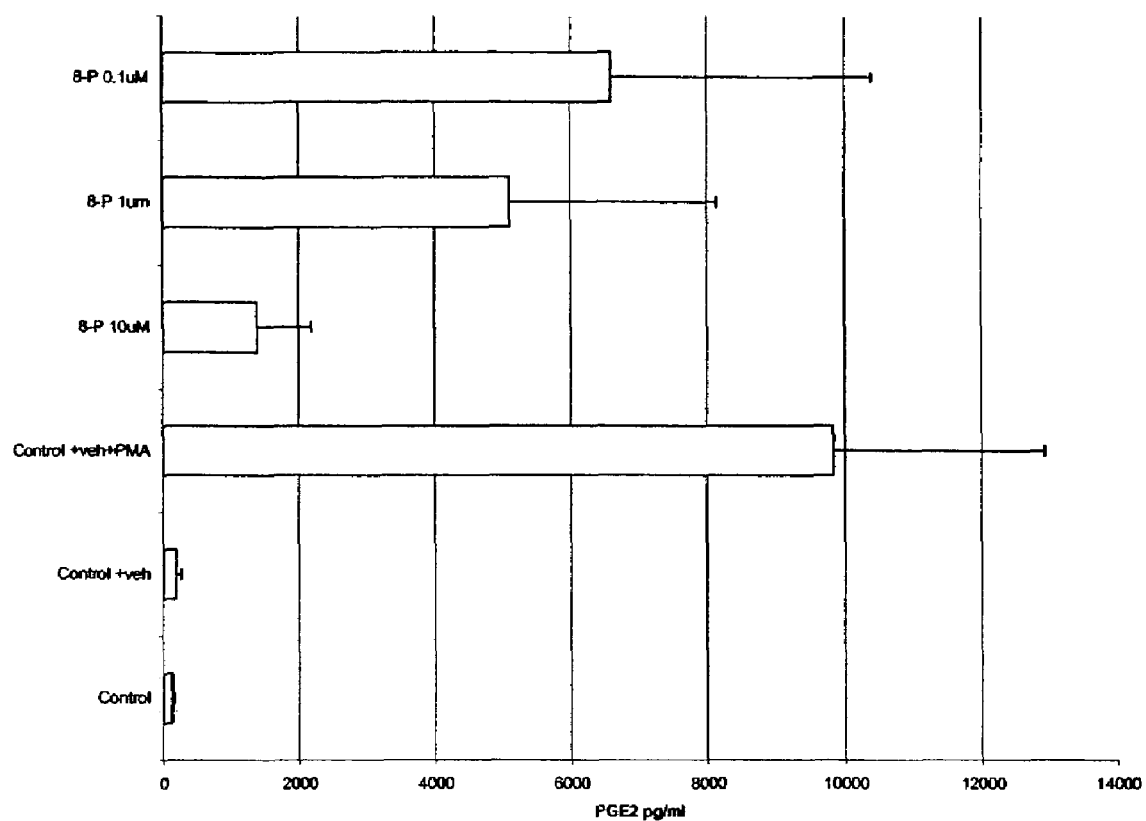

The effect of 8-prenylnaringenin on the reduction of PGE2 expression

The effect of 8-prenylnaringenin
on decorin synthesis in skin

The effect of 8-prenylnaringenin on procollagen-1 synthesis in skin

USE OF PRENYLATED FLAVONES

This is a divisional of Ser. No. 09/957,325 filed Sep. 20, 2001, now U.S. Pat. No. 6,589,982.

Compositions containing prenylated flavones are well known. According to prior art a great number of health effects are attributed to prenylated flavones and in particular to flavones with an isoprenyl substituted in the 8 position. Examples of references wherein these compounds and the health effects can be found are EP 667 289 wherein a number of humulones isolated from hop extracts are disclosed in relation to benefits in the bone/osteoporosis area. From Planta Med, 64 (1998) p. 516–9 and p. 511–5 it is known that 8-prenylnaringenin has beneficial bone effects. This compound is isolated from the heartwood of Anaxag Luzon. It is emphasized herein that in particular the position of the isoprenyl group in the flavone (i.e. the 8 position gives the best results) has a big impact on the performance of the compound. Another wellknown effect of the 8-prenyl flavones is their estrogenic activity. (cf: Tekel in J. of Agr and Food Chem 47, 1999, p. 5059–5063). Other effects of these flavones mentioned in the prior art are effects on arthritis or skin (JP 04202138), antibacterial effects (GB 2 330 076), antidiabetic activity (JP 83009084); anti cancer activity (Food and Chem Toxicology 37, 1999, p. 271–285) and an activity on lipid metabolism (J of the Amer Soc of Brewing Chem 56, 1998, p. 136–145). According to JP 11 246 387 (publication number) hop-extracts have elastase inhibiting activity and can be used to keep the skin taut and elastic. The extracts can be used in cosmetics and in bath liquids. The actual composition of the hop extracts is not given, therefore it remains uncertain what components will be present in the extract. This could be a wide variety of components depending on the exact conditions applied during the extraction.

Anti-inflammatory effects of prenylated flavones, such as Kuwanon C are disclosed in Chem. and Pharm. Bull. (Tokyo) 34, 1986, p. 1223–1227 and more generic in WO 00/33824, however no relation is disclosed between these effects and the presence of 8-prenylnaringenin or other 8-prenylated flavones.

We studied whether the 8-prenyl flavones (also indicated as flavonoids) still had other useful benefits and we found that these compounds indeed have another beneficial activity i.e. they are very useful as anti-inflammatory agents and as agents with skin benefits, in particular for promoting collagen-I and decorin synthesis. They thus can be used to treat/to prevent or to cure inflammatory diseases or skin disorders in mammals. Although anti-inflammatory and skin promoting agents are well known it was not known that the 8-prenyl flavones also possessed very high anti inflammatory or skin promoting activity. Skin promoting activity being defined as the ability of up-regulation of procollagen and decorin synthesis or of analogues thereof. This finding therefore extends the choice in the agents that can be used to treat/to prevent or to cure inflammatory diseases or skin disorders significantly. It is important to have the broadest choice possible in agents with a health effect because this will enable the consumer to use the agent that suits him/her best, moreover the prenylated compounds that can be used according to our invention are natural compounds, contrary to many of the known agents. We prefer to apply for our aims 8-prenylated flavones that are derived from hop and that are present in hop extracts in relatively large amounts.

We found that the most beneficial effects were achieved by applying 8-prenylnaringenin.

The prenylated flavones that can be used according to the invention can be applied in different ways. A very convenient way to apply these components for our purposes is to incorporate the flavone in a food product and to administer the food product to the person in need of these flavones. We found that these compounds can be incorporated into food products without destroying the product performance of the food product. Examples of food products that can be made with our flavones are spreads, creams, sauces, ice creams, mayonnaise's, dressings, confectionery products, fillings, bars, coatings, cereals, drinks. Apart from using a food wherein the flavones are incorporated we found that it also possible to use food supplements and to encapsulate the active ingredient (=flavones) in an encapsulating material. This material must of course be food acceptable. Suitable materials can be selected from the group consisting of sugars, polycarbohydrates, flour, starches, modified starches, gelatin, gums, pectin.

The amount of prenylated flavone that must be provided to the user can vary widely over a big range. However very suitable is that these flavones can be supplied to the consumer in amounts corresponding with the Recommended Daily Amount (=RDA) via 1 to 5 servings (food or supplement) per day.

Very useful amounts wherein the flavones are supplied to the customer range from 0.5 µg to 200 mg per serving of product.

According to another embodiment of our invention our invention also concerns with food products wherein the prenylated flavones are incorporated. These food products can contain all conventional ingredients for a food composition such as water fat, flour, polycarbohydrates, starches, modified starches.

The prenylated flavones are present in our food products in amounts of 0.5 □g to 200 mg per product.

Examples of food products that can be made in accordance with our invention are products selected from the group consisting of spreads, creams, sauces, ice creams, mayonnaise's, dressings, confectionery products, fillings, bars, coatings cereals, drinks.

In addition to the components mentioned above the food product can also contain micronutrients. Useful micronutrients can be selected from the group consisting of vitamins A, B, C, E, K, minerals, folic acid, magnesium, iron, copper, zinc, and conjugated fatty acids such as conjugated linoleic acid (CLA).

According to a last embodiment our invention concerns a method for treating/preventing/curing of inflammatory diseases or obtaining skin benefits in mammals as set out above by administering to the mammal an effective amount of one or more flavones with an prenyl group substituted in the 8 position. The effective amount suitably corresponds with the RDA that can be served by serving the mammal 1 to 5 portions of food per day.

EXAMPLES

Example 1

An ice cream was prepared according to the following recipe

| | Wt % |
|---|---|
| 8-Prenyl naringenin | 0.02 |
| Fat blend | 10.0 |
| Skimmed milk powder | 10.0 |

-continued

| | Wt % |
|---|---|
| Icing sugar | 12.0 |
| Corn syrup solids | 4.0 |
| Dextrose monohydrate | 2.0 |
| Sherex IC 93300 | 0.6 |
| Water added to total of | 100 |

Sherex IC 93300 is a product from Quest International and comprises mono- and diglycerides mixed with different stabilizers.

All ingredients except the water and the fat are mixed. Then the cold water is added to this mixture. This mixture is heated in a water bath till a temperature of 70° C. Then the fully liquid palm oil (=PO) is added to the mixture while "stirred" in the ultra-turrax. This emulsion is cooled in a water bath of 20° C. The emulsion is stirred in the ultra-turrax again. The batch ice cream machine is held for 24 hours at −28° C. prior to use. The emulsion is placed in the batch ice cream machine and stirred for 15 minutes. The resulting ice cream is stored at −20° C. for 24 hours and then evaluated. The viscosity of the ice cream emulsion, prior to freezing is measured. The overrun and hardness are determined. The viscosity is measured by using the Haake viscometer. Hardness is measured by using a Stevens texture analyser with a 450 cone at a speed of 0.5 mm/second till a deepness of 2 mm.

The ice cream obtained is of excellent quality.

Example 2

A spread containing 8-Prenyl naringenin is prepared:
The following ingredients were used in the process described below:

| | wt % |
|---|---|
| 8-Prenylnaringenin | $5 \times 10^{-3}$ |
| Oil blend | 49.5 |
| Lecithin | 0.205 |
| distilled monoglyceride | 0.3 |
| Flavour | 0.01 |
| Colour | 0.0066 |
| Whey | 0.25 |
| EDTA | 0.007 |
| Citric Acid | 0.03 |
| K Sorbate | 0.1 |
| Salt | 1.6 |
| Water to make it to | 100% |

The fat and aqueous phases are mixed together at approximately 55° C. in a heated tank in a ratio of approximately 40 parts fat phase to 60 parts aqueous phase. This emulsion will be fat continuous. Aqueous phase is added to the fat phase to aid in obtaining a fat continuous emulsion in the tank.

The emulsion is then passed through a cooled, scraped-surface heat exchanger (A-unit) where the emulsion is cooled to a temperature where the fat will begin to crystallize (about 8–20° C.) and the aqueous phase will begin to increase in viscosity. The cooled emulsion is then passed through a C-unit, crystallizer. The shaft speed may vary and depends on it's dimensions and the residence time required to crystallize the fat in line but normally varies from 100–900 RPM. The fat continuous emulsion is passed into an additional cooling unit to reduce the temperature of the emulsion since there is a temperature rise due to heat of crystallization in the crystallizer. Depending on the final product, for a tub product, the cooled emulsion is passed through the crystallizer (C-Unit) to provide additional residence time and adjust the consistency for packaging in tub. For a stick product, the cooled emulsion is be passed through a B-Unit for additional residence time and to increase the packing hardness for the product to be packed in the stick form. The products that are obtained are of excellent quality Methodology Anti-inflammatory cell assays It is emphasized that the anti-inflammatory effects were determined by in vitro tests wherein the Prostaglandin E2 (=PGE2) production by the human skin fibroblasts is measured after being induced by the inflammatory modulus phorbyl myristyl acetate (PMA). A reduction of the levels of PGE2 is indicative for the anti-inflammatory effect.

Fibroblast cell assay Primary human foreskin fibroblasts at passage 2 (P2) were seeded into 96-well plates at 35000 cells/well and maintained for 24 hours in an atmosphere of 5% carbon dioxide in Dulbeccos Modified Eagles Medium (DMEM) supplemented with 10% foetal calf serum. 8-Prenyl naringenin was added to fresh cell media (DMEM, supplemented with 10% foetal calf serum) in 100% ethanol (final concentration 1%) in triplicate and incubated for a further 24 hours. Phorbal myristate acetate (PMA) in ethanol/cell media (10 nm) was added to the media and the cells incubated for a further 24 hours. PMA represents an external stressor, which induces oxidative stress and inflammatory responses in cells. The fibroblasts/media were then analysed as described below immediately or snap frozen in liquid nitrogen and stored at −70° C. for future analysis. The cells were then counted to ensure no effect on cell number.

Prostaglandin E2 (PGE2) assay Volumes of 50 µl culture medium were taken for PGE2 assay after gently shaking the culture plate. PGE2 levels in the medium were determined with a Biotrak PGE2 immunoassay kit (Amersham, UK). The assay is based on the competition between unlabelled PGE2 in the sample and a fixed quantity of horseradish peroxidase labelled PGE2 for a limited amount of fixed PGE2 specific antibody. Concentrations of unlabelled sample PGE2 are determined according to a standard curve, which was obtained at the same time. The results are demonstratd in FIG. 1.

Procedure for Measuring Procollagen-I and Decorin Synthesis in Human Dermal Fibroblasts Preparation of Dermal Fibroblast Conditioned Medium Primary human foreskin fibroblasts at passage 2 (P2) were seeded into 12-well plates at 40000 cells/well and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagent (8-Prenyl naringenin at different levels) and vehicle control (1% ethanol final concentration) were added to the cells in triplicate in a final volume of 0.4 ml/well fresh serum free DMEM and incubated for a further 24 hours. This fibroblast conditioned medium was either analysed immediately or snap frozen in liquid nitrogen and stored at −70° C. for future analysis. The cells were then counted and data from the dot-blot analysis subsequently standardised to cell number.

Figure 2:
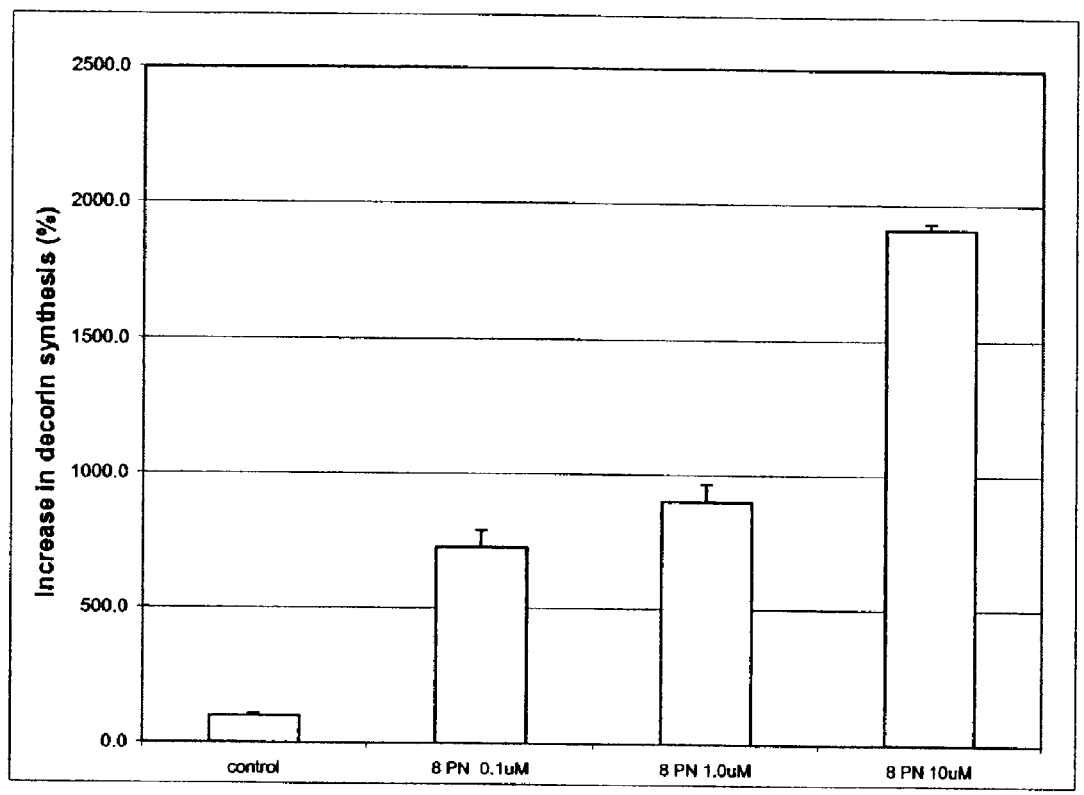
Figure 3:
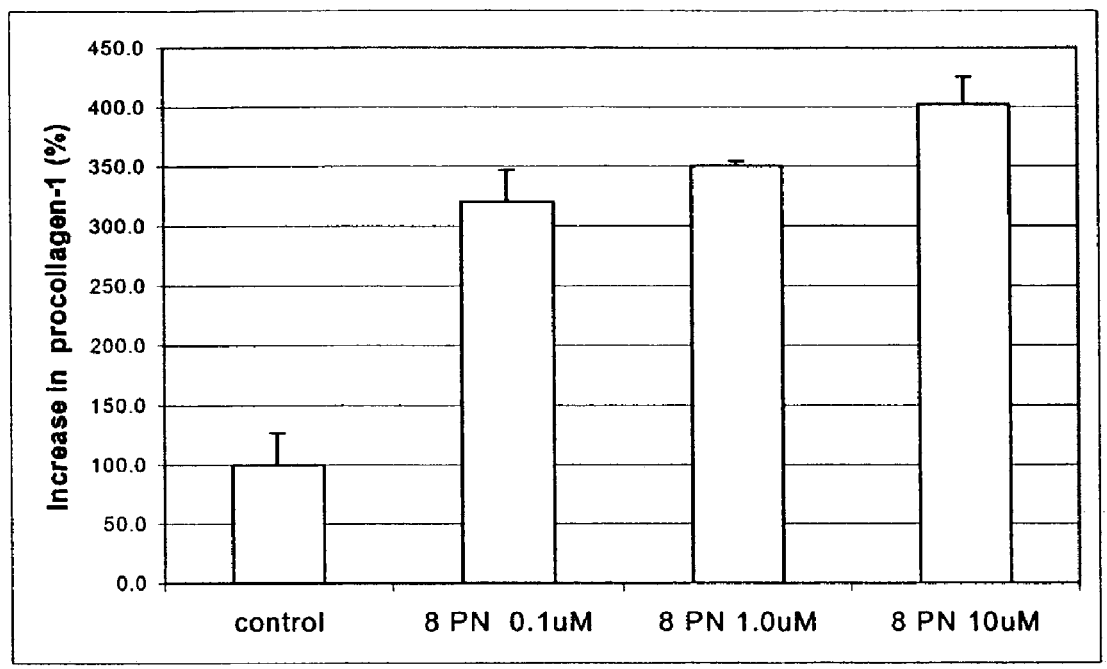

Dot Blot Assay for Decorin Protein in Dermal Fibroblast Conditioned Medium Samples of conditioned medium from dermal fibroblasts treated with vehicle (as a control) or test reagent were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10000 cells/cm$^2$ in a 175 cm$^2$ flask and maintained in serum free DMEM as described above. Assay samples were subsequently applied in triplicate to a prewetted sheet of Immobilon-P transfer membrane using the 96-well Bio-Dot Apparatus from Bio-Rad as described in the manufacturers guidelines. Approximately 200 µl of medium was applied per well. The medium was allowed to filter through the membrane under gravity (30 minutes) after which the membrane was washed twice with PBS (200 µl). These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for decorin analysis were blocked with 3% (w/v) bovine serum albumin (BSA)/0.1% (v/v) Tween 20 in phosphate buffered saline (PBS), whilst those for procollagen-I analysis were blocked with 5% (w/v) non fat dried milk powder/0.05% Tween 20 in PBS. The following day, the membranes were probed with 1:10000 dilution of primary antibodies to human decorin (rabbit polyclonal; Biogenesis) for 2 hours at room temperature. The membranes were subsequently washed with TBS/0.05% Tween 20 (3×15 minutes) and then incubated with 1:1000 dilution of $^{125}$I-conjugated anti-rat or anti-rabbit F(ab')2 fragments (Amersham) as required for 1 hour at room temperature. Following this the Immobilon strips were again washed with TBS/Tween 20 (3×15 minutes) before being allowed to dry in air at room temperature. The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of various test reagents on decorin and procollagen-I synthesis were determined relative to a vehicle treated control value of 100 arbitrary units. The results are illustrated in FIGS. 2 and 3.

The invention claimed is:

1. Food product comprising in addition to one or more conventional food ingredients selected from the group consisting of water, fat, flour, polycarbohydrates, and starches; an 8-prenylated flavone present at 0.005 wt % to 0.02 wt % in the product, wherein the 8-prenylated flavone is capable of providing an anti-inflamatory effect and/or promoting the synthesis of collagen and/or decorin.

2. The food product according to claim 1 wherein the 8-prenylated flavone is 8-isoprenylnaringenin.

3. Food products according to claim 1, wherein the food product is selected from the group consisting of spreads, creams, sauces, ice creams, mayonnaise's, dressings, confectionery products, fillings, bars, coatings, cereals and drinks.

4. Food products according to claim 1, wherein the food products also contains an effective amount of a micronutrient selected from the group consisting of vitamins A, B, C, E, K, minerals, folic acid, magnesium, iron, copper, zinc, calcium and conjugated fatty acids.

* * * * *